United States Patent [19]

Sugihara et al.

[11] Patent Number: 4,695,354
[45] Date of Patent: Sep. 22, 1987

[54] MEDIUM FOR ELECTROPHORESIS

[75] Inventors: Mitsuru Sugihara; Naohiko Sugimoto, both of Asaka, Japan

[73] Assignee: Fuji Photo Film Co., Ltd., Kanagawa, Japan

[21] Appl. No.: 908,376

[22] Filed: Sep. 17, 1986

[30] Foreign Application Priority Data

Sep. 18, 1985 [JP] Japan ............................... 60-206090

[51] Int. Cl.$^4$ ....................... G01N 27/26; C08K 5/21; B01K 5/00
[52] U.S. Cl. .............................. 204/180.1; 204/182.8; 528/317
[58] Field of Search .................. 204/180.1, 182.8; 528/317

[56] References Cited

U.S. PATENT DOCUMENTS

| 3,497,437 | 2/1970 | Louderback et al. | 204/182.8 |
| 4,319,975 | 3/1982 | Cook | 204/182.8 |
| 4,319,976 | 3/1982 | Gurske | 204/182.8 |
| 4,321,121 | 3/1982 | Gurske | 204/182.8 |
| 4,548,869 | 10/1985 | Ogawa et al. | 204/182.8 |
| 4,548,870 | 10/1985 | Ogawa et al. | 204/182.8 |
| 4,559,120 | 12/1985 | Royse et al. | 204/182.8 |
| 4,579,783 | 4/1986 | Ogawa et al. | 204/182.8 |
| 4,582,868 | 4/1986 | Ogawa | 204/182.8 |
| 4,600,641 | 7/1986 | Ogawa | 204/182.8 |

FOREIGN PATENT DOCUMENTS 0137753 4/1985 European Pat. Off. .

Primary Examiner—Arthur P. Demers
Attorney, Agent, or Firm—Jules E. Goldberg

[57] ABSTRACT

In a medium for electrophoresis suitably employable for determination of base sequence of DNA, RNA, their fragments, and their derivatives, which comprises an aqueous polyacrylamide gel formed by crosslinking polymerization of an acrylamide compound and a crosslinking agent in the presence of water and at least one compound having a carbamoyl group, the improvement wherein glycerol is contained in the medium in a small amount ranging from 0.1 to 1.0 wt/v %.

3 Claims, 2 Drawing Figures

MEDIUM FOR ELECTROPHORESIS

BACKGROUND OF OF THE INVENTION

1. Field of the invention

This invention relates to a medium for electrophoresis, and more particularly relates to a medium for electrophoresis suitably employable for the determination of base sequence of DNA, RNA, their fragments, and their derivatives.

2. Description of prior art

For the determination of base sequence of DNA or RNA according to a chemical decomposition method and a dideoxy method, the slab electrophoresis using an aqueous polyacrylamide gel membrane (or medium) is necessarily employed. The aqueous polyacrylamide gel membrane employed for the above purpose is generally prepared by crosslinking polymerization of approx. 95 weight parts of a monomer such as acrylamide and approx. 5 weight parts of a two(or more)-functional crosslinking agent such as N,N'-methylenebisacrylamide in an aqueous solution (concentration: approx. 3 to 30 wt. %).

At the present time, it is desired to make a thinner gel membrane so as to enhance the resolving power for resolving nucleic acid fragments. However, if the conventionally employed polyacrylamide gel membrane is made thinner in its thickness, such gel membrane gives a distorted resolved pattern as illustrated schematically in FIG. 2. FIG. 2 shows that resolution bands 2, each 1 of the bands corresponding to nucleic acid fragments having high molecular weight excessively extend in the width direction with distortion of the band shape. Such distorted bands make it difficult to read the resolved pattern.

Japanese Patent Provisional Publication 60(1985)-60548, etc. disclose that glycerol can be incorporated into a gel membrane as a wetting agent in an amount of approx. 1 to 40 wt/v %. However, the incorporation of glycerol as a wetting agent is considered to require a relatively great amount because incorporation of glycerol in a small amount near to the above lower limit shows too low wetting effect. The incorporation of glycerol into the gel membrane in an excessively great amount is not favorable because such incorporation makes the membrane so soft and extensile as to decrease handling efficency.

SUMMARY OF THE INVENTION

It has been now discovered that incorporation of glycerol in a small amount of lower than 1 wt/v % into an aqueous polyacrylamide gel medium (membrane) is very effective to reduce the above-mentioned extension in the width direction and distortion of resolved bands.

An object of the present invention is to provide a medium for electrophoresis which is suitably employable for the determination of base sequence of DNA, RNA and analogous polymers.

Another object of the invention is to provide a medium for electrophoresis which is improved in the resolving power so that the extension of the bands (i.e., each pattern of fragment) in the width direction and distortion of the bands are effectively reduced.

A further object of the invention is to provide a medium for electophoresis which can be made to have a very thin thickness without decrease of the resolving power.

A still further object of the invention is to provide a medium for electrophoresis which is stable in size and can be easily handled.

There is provided by the present invention the improvement of a medium for electrophoresis comprising an aqueous polyacrylamide gel formed by crosslinking polymerization of an acrylamide compound and a crosslinking agent in the presence of water and at least one compound having a carbamoyl group, wherein glycerol is contained in the medium in an amount ranging from 0.1 to 1.0 wt/v % (i.e., 0.1 to 1.0 weight/volume %).

The medium for electrophoresis containing a small amount of glycerol which is according to the present invention shows a satisfactory resolved pattern in the electrophoresis of nucleir acids and related substances. For instance, the resolved bands corresponding to fragments having a high molecular weight are free from or almost free from extension in the width direction and distortion. Therefore, the use of the medium according to the invention in the determination of base sequence of DNA and analogous polymers is very favorable because the resolution of the resolved bands is prominently enhanced. Further, the medium of the invention has a relatively high elasticity and hence is hardly deformed in the handling. This property is of remarkable value when the medium is formed to have a thin thickness.

DETAILED DESCRIPTION OF THE INVENTION

Figure 1:
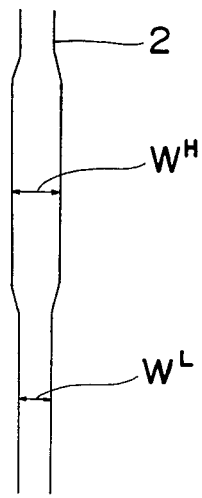
FIG. 1 shows the problem of a conventional thin aqueous polyacrylamide gel medium in which resolution bands corresponding to nucleic acid fragments having high molecular weight excessively extend in the width direction with distortion of the band shape.
Figure 2:
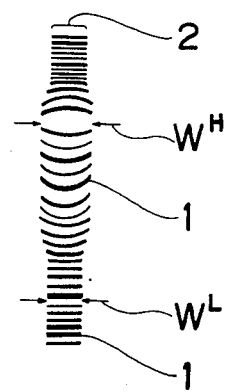
FIG. 2 shows a resolved pattern formed using an electrophoretic medium according to the present invention.

The medium for electrophoresis of the invention can be prepared on a support, and is generally preserved, transported and handled on the support. However the support having been used in the preparation of the medium may be replaced with other material before the medium is preserved, transported or handled.

Examples of the support employable for the preparation of the medium for electrophoresis of the invention include a variety of transparent waterproof materials in the form of sheet (the term "sheet" includes a film and a plate), such as glass board, polymer coated paper, a plastic material. However, a plastic material sheet is advantageously employed for the medium for electrophoresis of the present invention.

Examples of the support of the plastic material sheet employable for the medium for electrophoresis include a variety of polymer materials in the form of sheet. Examples of the polymer materials include polyethylene terephthalate, polycarbonate of Bisphenol A, polyvinyl chloride, vinylidene chloride-vinyl chloride copolymer, polymethyl methacrylate, polyethylene, polypropylene, cellulose acetates, and cellulose acetate propionate. Preferred is a polyethylene terephthalate sheet. The support of the plastic material can be processed by irradiation of ultra-violet rays, glow discharge, corona discharge, flame, irradiation of electron beam, chemical etching, or electrolytic etching for making the surface of the support hydrophilic to enhance adhesion between the support and the aqueous polyacrylamide gel medium to be placed thereon. The surface of the plastic support may be coated with a subbing layer or an adhesive layer such as those described in Japanese Patent Provisional Publications No. 59(1984)-164950 and No. 59(1984)-212752, and Japanese Patent Applications No. 59(1984)-50294, No. 59(1984)-96152, No. 59(1984)-136247, No. 59(1984)-103307, etc.

The support has a thickness generally in the range of approx. 50 μm to approx. 1 mm, preferably in the range of approx. 80 to 500 μm.

The aqueous gel medium layer is now described in more detail.

The aqueous gel medium (may be referred to herein as "gel membrane") employed in the invention is a medium or a medium layer consisting essentially of an aqueous polyacrylamide gel formed by crosslinking polymerization of an acrylamide compound and a crosslinking agent in the presence of water, a compound having a carbamoyl group and a small amount of glycerol.

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the acrylamide compound employable in the present invention include acrylamide and its homologues such as N-methylacrylamide, N,N-dimethylacrylamide, N-(hydroxymethyl) acrylamide and diacetonacrylamide, as well as methacrylamide and its homologues. These compounds can be empolyed independently or in combination. Acrylamide is most preferred among these acrylamide compounds, and said acrylamide can be also preferably employed in combination with one or more of other acrylamide compounds.

The crosslinking agent of the invention is a compound having two or more reactive groups. Examples of the crosslinking agents include difunctional compounds such as N,N'-methylenebisacrylamide (BIS), N,N'-propylenebisacrylamide (PBA), diacrylamide diemthyl ether (DAE), 1,2-diacrylamide ethyleneglycol (DEG), ethyleneurea-bisacarylamide (EUB), ethylene diacrylate (EDA), N,N'-diallyltartardiamide (DATD) and N,N'-bisacrylylcystamine (BAC), and trifunctional compounds such as triallylcyanurate(TAC), triallylisocyanurate (TAIC) and 1,3,5-triacryloylhexahydro-s-triazine (TAHT). Known bifunctional crosslinking agents are described, for instance, in "Electrophoresis" 1981, 2, 213-228. The trifunctional crosslinking agents are described in Japenese Patent Application No. 59(1984)-122662. The crosslinking agents can be employed singly or in combination.

The crosslinking agent can be employed in an amount of approx. 1 to 30 wt. %, preferably approx. 2 to 10 wt. %, based on the total weight of the monomer (i.e., acrylamide compound) and the crosslinking agent.

The gel membrane may contain agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB No. 2 042 571A), 57(1982)-502098 (WO No. 82/02599, U.S. Pat. No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent.

The gel membrane of the invention may contain a water-soluble polymer. As the water-soluble polymer, a water-soluble polymer of the addition polymerization type of condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. Water-soluble polymers of a molecular weight ranging from approx. 10,000 to 1,000,000 stated in Japanese Patent Provisional Publications No. 59(1984)-126236 and No. 60(1985)-60548 are preferably used. Among these water-soluble polymers, polyacrylamide and polyethylene glycol are preferable. The water-soluble polymer is used in the range of approx. 2 to 100 wt. %, preferably, approx. 5 to 50 wt. %, based on the total weight of the monomer and crosslinking agent.

The electrophoretic medium of the invention contains a compound having at least one carbamoyl group as a modifier. Examples of the modifiers include urea and formamide. Urea is most preferred. The modifier can be used in an amount of approx. 40 to 60 wt. % based on the volume of the aqueous gel containing the monomer and crosslinking agent. In the case that urea is used as the modifier, the amount generally ranges from approx. 6 moles (approx. 360 g.) per one liter of the aqueous gel containing the monomer 7 and crosslinking agent to the saturation amount, preferably from approx. 7 moles (approx. 420 g.) to the saturation amount.

The characteristic feature of the invention resides in the incorporation of a small amount of glycerol in the aqueous polyacrylamide gel membrane. The amount of glycerol is in the range of approx. 0.1 wt/v % to approx. 1.0 wt/v %, preferably in the range of approx. 0.3 wt/v % to approx. 0.8 wt/v %. Glycerol is preferably incorporated into the membrane in the course from the stage for dissolving the monomer and crosslinking agent in water to the stage for formation of an aqueous gel.

A pH buffer agent can be contained in the gel membrane of the invention.

In the medium for electrophoresis of DNA and the like, a buffer agent which is able to buffer a solution to a range of pH 8.0 to 9.0, preferably pH 8.2 to 8.3 can be incorporated. Examples of the buffer agent include tris (hydroxymethyl) aminomethane (Tris), N,N-bis(2-hydroxyethyl)glycine (Bicine), N-2-hydroxyethyl-piperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl]-3-aminopropanesulfonic acid (TAPS) or its Na or K salt; as well as an acid, an alkali, and a salt employable in combination with the compounds. Preferable examples of the buffer agent include Tris, boric acid-EDTA.2Na (pH 8.2–8.3).

The gel membrane of the invention is formed by radical crosslinking polymerization between the monomer such as acrylamide with a crosslinking agent in an aqueous medium in which glycerol is preferably dissolved almost homogeneously.

The crosslinking polymerization can be initiated by a known method, for instance, in the presence of a polymerization catalyst and/or under irradiation of ultra-violet rays. The reaction can be further accelerated by heat and irradiation with ultraviolet rays.

As the polymerization catalyst, a known low temperature-polymerization initiator such as those described in "Electrophoresis" 1981, 2, 213–219, ibid. 1981, 2, 220–228; and "Modern Electrophoresis" edited by Aoki & Nagai (Hirokawa Shoten, 1973) can be used. Examples of the initiator include a mixture of β-dimethylaminopro-pionitrile (DMAP) and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultraviolet rays. The radical reaction initiator can be employed in the amount of approx. 0.3 to 5 wt. %, preferably approx. 0.5 to 3 wt. %, based on the total amount of the monomer and crosslinking agent.

The gel concentration of the aqueous polyacrylamide gel medium of the invention preferably is in the range of approx. 3 to 30 wt/v % (total weight of monomer and crosslinking agent per total volume of gel membrane comprising monomer, crosslinking agent and aqueous medium), the concentration being expressed in accordance with the definition indicated by S. Hjerten in Arch. Biochem. Biophys. 1 (Suppl.), 147 (1962).

The gel membrane of the medium of the invention can be prepared by a process in which a gel forming solution is coated by a known method on an electric insulation support having an adhesive layer. The gel forming solution is then crosslinked to polymerization on the surface of the support under an inert condition.

In the case the gel forming solution is crosslinked on the surface of the support, the surface of the gel forming solution layer can be covered with a covering material such as a film, sheet, or plate. The same material as employable for the support can be employed as the covering material. The covering materials may be previously so treated by glow discharge treatment to have a hydrophilic surface. The covering material has thickness of not more than 300 μm, and preferably has approx. 4 to 200 μm, more preferably approx. 4 to 100 μm, from the practical viewpoint.

The aqueous polyacrylamide gel medium of the invention has thickness generally in the range of approx. 50 μm to approx. 5 mm, preferably in the range of approx. 80 to 500 μm. The gel membrane of the invention can be made very thin without deterioration of resolving power. Accordingly, the gel membrane can be made very thin to have a thickness in the range of approx. 50 to 300 μm.

The gel membrane of the invention can be employed for the horizontal or vertical electrophoresis, disc electrophoresis, etc. by known methods described, for instance, in the aforementioned texts.

The present invention will be more clearly understood with reference to the following examples.

EXAMPLE 1 & COMPARISON EXAMPLE 1

A rectangular glass plate (support, thickness: 2 mm, size: 20 cm×40 cm) having a smooth surface was placed horizontally, and on the circumferential area were fixed spacers (thickness: 200 μm, width: 10 mm). The glass plate was coated with a gel-forming solution having the composition set forth in Table 1. Another glass plate of the same size was placed on the coated layer, and the coated layer was allowed to stand for performing crosslinking polymerization reaction between the two glass plates. Thus, an aqueous polyacrylamide gel membrane of 200 μm thick was prepared.

Evaluation of the gel membrane was made on the determination of base sequence of DNA using a sample prepared by a dioxy method and according to the conventional method.

It was confirmed that the gel membrane (1) of the invention containing 0.5 wt/v % of glycerol showed satisfactory resolved pattern 2, as schematically illustrated in FIG. 1. In more detail, the ratio of width ($W^H$) of bands corresponding to fragments having a high molecular weight in the resolved pattern 2 to the width ($W^L$) of bands corresponding to fragments having a low molecular weight observed on the resolved pattern was 1.05 (average value), and extension of the bands in the width direction and distortion of the bands were minimized so as to read the resolved pattern very accurately. In contrast, the gel membrane (2) according to the conventional art containing no glycerol showed the ratio ($W^H/W^L$) of 1.13 (average value), and extension of the bands in the width direction and distortion of the bands were prominent so as to disturb reading of the resolved pattern. Accordingly, it has been confirmed that the gel medium of the invention shows an improved resolving power for the resolution of fragments of a high molecular weight.

TABLE 1

| (Composition of Gel Forming Solution for Gel Medium) | | |
|---|---|---|
| Sample No. | 1 (For Invention) | 2 (For Comparison) |
| Acrylamide | 7.6 g. | 7.6 g. |
| BIS | 0.6 g. | 0.6 g. |
| Urea | 42.0 g. | 42.0 g. |
| Glycerol | 0.5 g. | None |
| pH Buffer | | |
| Tris | 1.21 g. | 1.21 g. |
| Boric acid | 0.65 g. | 0.65 g. |
| EDTA.2Na | 75 mg. | 75 mg. |
| Addition of water to | 100 ml | 100 ml |
| Polymerization initiator | | |
| Ammonium peroxodisulfate (5 wt. % aq. sol.) | 1.3 ml. | 1.3 ml. |
| TEMED (25 wt. % aq. sol.) | 33 μl. | 33 μl. |

In Table 1, BIS represents N,N'-methylenebis-acrylamide, Tris represents tris(hydroxymethyl)aminomethane, and TEMED represents N,N,N',N'-tetramethylethylenediamine.

EXAMPLE 2 & COMPRAISON EXAMPLE 2

A rectangular polyethylene terephthalate (PET) sheet (support, thickness: 180 μm, size: 20 cm×40 cm) having a smooth surface which had been made hydrophilic by irradiation of ultra-violet rays was placed horizontally, and on the circumferential area were fixed spacers (thickness: 200 μm, width: 10 mm). The support was coated with a gel-forming solution having the composition set forth in Table 2, and the coated layer was allowed to stand for performing crosslinking polymerization reaction in a nitrogen atmosphere. Thus, an aqueous polyacrylamide gel membrane of 200 μm thick was prepared.

Evaluation of the gel membrane was made on the determination of base sequence of DNA in the same manner as in Example 1.

It was confirmed that the gel membrane (3) of the invention containing 0.5 wt/v % of glycerol showed satisfactory resolved pattern. In more detail, the ratio ($W^H/W^L$) was 1.18 (average value), and extension of the bands in the width direction and distortion of the bands were minimized so as to read the resolved pattern very accurately. In contrast, the gel membrane (5) according to the conventional art containing no glycerol showed the ratio ($W^H/W^L$) of 1.45 (average value), and extension of the bands in the width direction and distortion of the bands were abnormally prominent so as to disturb reading of the resolved pattern.

The gel membrane (4) according to the known art containing 2.0 wt/v % of glycerol showed the ratio ($W^H/W^L$) of 1.10 (average value), and extension of the bands in the width direction and distortion of the bands were minimized so as to read the resolved pattern accurately. However, the gel membrane (4) showed very low elasticity such as modulus of elasticity (unit: $N/cm^2$) of 1.3, as compared with that of 1.7 for the gel membranes (3) and (5). Accordingly, the gel membrane (4) was not appropriate for handling because it was easily deformed in the handling.

Therefore, it has been confirmed that the gel medium of the invention shows an improved resolving power for the resolution of fragments of a high molecular weight with no deterioration of workability.

TABLE 2

(Composition of Gel Forming Solution for Gel Medium)

| Sample No. | 3 (For Invention) | 4 (For Comparison) | 5 |
|---|---|---|---|
| Acrylamide | 7.66 g. | 7.66 g. | 7.66 g. |
| TAHT | 0.34 g. | 0.34 g. | 0.34 g. |
| Urea | 42.0 g. | 42.0 g. | 42.0 g. |
| Glycerol | 0.5 g. | 2.0 g. | None |
| pH Buffer | | | |
| Tris | 1.21 g. | 1.21 g. | 1.21 g. |
| Boric acid | 0.65 g. | 0.65 g. | 0.65 g. |
| EDTA.2Na | 75 mg. | 75 mg. | 75 mg. |
| Addition of water to | 100 ml | 100 ml | 100 ml |
| Polymerization initiator | | | |
| Ammonium peroxodisulfate (5 wt. % aq. sol.) | 1.3 ml. | 1.3 ml. | 1.3 ml. |
| TEMED (25 wt. % aq. sol.) | 33 μl. | 33 μl. | 33 μl. |

In Table 2, Tris represents tris(hydroxymethyl)-aminomethane; TAHT represents 1,3,5-triacryloylhexahydro-s-triazine; and TEMED represents N,N,N',N'-tetramethylethylenediamine.

EXAMPLE 3 & COMPARISON EXAMPLE 3

The procedure of Example 2 was repeated except that the thickness of the spacer was changed to 150 μm and the coating solution for the preparation of gel medium contained agarose to prepare an aqueous polyacrylamide gel membrane of 150 μm thick was prepared.

Evaluation of the gel membrane was made on the determination of base sequence of DNA in the same manner as in Example 1.

It was confirmed that the gel membrane (6) of the invention containing 0.5 wt/v % of glycerol showed satisfactory resolved pattern. In more detail, the ratio ($W^H/W^L$) was almost the same as that for the gel membrane 3 in Example 2, and extension of the bands in the width direction and distortion of the bands were minimized so as to read the resolved pattern very accurately. In contrast, the gel membrane (7) according to the conventional art containing no glycerol showed the ratio ($W^H/W^L$) being almost the same as that for the gel membrane 5 in Example 2, and extension of the bands in the width direction and distortion of the bands were prominent so as to disturb reading of the resolved pattern. Accordingly, it has been confirmed that the gel medium of the invention shows an improved resolving power for the resolution of fragments of a high molecular weight.

TABLE 3

(Composition of Gel Forming Solution for Gel Medium)

| Sample No. | 6 (For Invention) | 7 (For Comparison) |
|---|---|---|
| Acrylamide | 7.66 g. | 7.66 g |
| TAHT | 0.34 g. | 0.34 g. |
| Agarose | 0.45 g. | 0.45 g. |
| Urea | 42.0 g. | 42.0 g. |
| Glycerol | 0.5 g. | None |
| pH Buffer | | |
| Tris | 1.21 g. | 1.21 g. |
| Boric acid | 0.65 g. | 0.65 g. |
| EDTA.2Na | 75 mg. | 75 mg. |
| Addition of water to | 100 ml | 100 ml |
| Polymerization initiator | | |
| Ammonium peroxodisulfate (5 wt. % aq. sol.) | 1.3 ml. | 1.3 ml. |
| TEMED (25 wt. % aq. sol.) | 33 μl. | 33 μl. |

In Table 3, TAHT, Tris and TEMED have the same meanings as described for Tables 1 and 2. Agarose was a low electro-endosmosis agarose (gelation temperature: 36° C.).

We claim:

1. In a medium for electrophoresis comprising an aqueous polyacrylamide gel formed by crosslinking polymerization of an acrylamide compound and a crosslinking agent in the presence of water and at least one compound having a carbamoyl group, the improvement wherein glycerol is contained in the medium in an amount ranging from 0.3 to 0.8 wt/v %.

2. The medium as claimed in claim 1, wherein the medium has a thickness in the range of 80 to 500 μm.

3. The medium as claimed in claim 1, wherein the medium has a thickness in the range of 50 to 300 μm.

* * * * *